US00PP11425P

United States Patent [19]

Dümmen

[11] Patent Number: Plant 11,425

[45] Date of Patent: Jun. 20, 2000

[54] NEW GUINEA IMPATIENS PLANT NAMED 'DUEPETHOPI'

[75] Inventor: Marga Dümmen, Rheinberg, Germany

[73] Assignee: Dummen Jungpflanenkulturen, Rheinberg, Germany

[21] Appl. No.: 09/103,179

[22] Filed: Jun. 22, 1998

[51] Int. Cl.[7] ..... A01H 5/00

[52] U.S. Cl. ..... Plt./318

[58] Field of Search ..... Plt./318

[56] References Cited

U.S. PATENT DOCUMENTS

P.P. 8,252 6/1993 Dehan ..... Plt./318
P.P. 8,870 8/1994 Trees ..... Plt./318

*Primary Examiner*—Howard J. Locker
*Assistant Examiner*—Wendy A. Baker
*Attorney, Agent, or Firm*—C. A. Whealy

[57] ABSTRACT

A new and distinct variety of New Guinea Impatiens plant named 'Duepethopi', characterized by its dark pink petal color; floriferousness; dense and bushy plant habit; very freely and basally branching plant habit; and medium green non-variegated foliage.

1 Drawing Sheet

BACKGROUND OF THE INVENTION

The present invention relates to a new and distinct variety of New Guinea Impatiens plant, botanically known as *Impatiens hawkeri*, and hereinafter referred to by the name 'Duepethopi'. The new variety is marketed under the trade name Red Fox Petticoat Hot Pink.

The new variety is a product of a planned breeding program conducted by the Inventor in Rheinberg, Germany. The objective of the breeding program is to develop New Guinea Impatiens that are freely branching; compact; early flowering; and that have desirable flower and leaf colors.

The new cultivar originated from a cross made by the Inventor of the proprietary New Guinea Impatiens seedling selection identified as code number S236 as the male or pollen parent with a proprietary New Guinea Impatiens seedling selection identified as code number S248 as the female or seed parent.

'Duepethopi' was discovered and selected in 1996 by the Inventor as a single flowering plant within the progeny of the stated cross in a controlled environment in Rheinberg, Germany.

Asexual reproduction of the new variety by terminal cuttings taken at Rheinberg, Germany, has shown that the unique features of this new variety are stable and reproduced true to type in successive generations of asexual reproduction.

BRIEF SUMMARY OF THE INVENTION

The following traits have been repeatedly observed and are determined to be the unique characteristics of 'Duepethopi'. These characteristics in combination distinguish 'Duepethopi' as a new and distinct variety:

1. Dark pink petal color.
2. Freely flowering.
3. Dense and bushy plant habit.
4. Very freely and basally branching plant habit.
5. Medium green non-variegated foliage.

In side-by-side comparisons conducted by the Inventor in Rheinberg, Germany, plants of the new New Guinea Impatiens are more compact and differ from the parent varieties in flower color.

The new variety can be compared to the commercial cultivar Dueripi (disclosed in U.S. Plant Pat. No. 11,079). However, in side-by-side comparisons conducted by the Inventor in Rheinberg, Germany, plants of the new variety are more compact and flower earlier than plants of the cultivar Dueripi.

BRIEF DESCRIPTION OF THE PHOTOGRAPH

The accompanying colored photograph illustrates the overall appearance of the new variety, showing the colors as true as it is reasonably possible to obtain in colored reproductions of this type. Colors in the photographs may differ slightly from the color values cited in the detailed botanical description which more accurately describe the actual colors of the new New Guinea Impatiens. The photograph comprises a side perspective view of a typical plant of 'Duepethopi'. Flower and foliage colors in the photograph may appear different from the actual color due to light reflectance.

DETAILED BOTANICAL DESCRIPTION

Plants of 'Duepethopi' have not been observed under all possible environmental conditions. The phenotype may vary somewhat with variations in environment such as temperature, daylength and light intensity, without, however, any variance in genotype. The following observations and measurements describe plants grown in 12-cm containers during the spring in Rheinberg, Germany, under commercial practice in a glass-covered greenhouse with day of about 22° C., night temperatures about 18° C. and light levels about 42.5 thousand lux.

In the following description, color references are made to The Royal Horticultural Society Colour Chart except where general terms of ordinary dictionary significance are used.

Botanical classification: *Impatiens hawkeri* 'Duepethopi'.

Parentage:

*Male, or pollen, parent.*—*Impatiens hawkeri* seedling selection, code number S236.

*Female, or seed, parent.*—*Impatiens hawkeri* seedling selection, code number S248.

Propagation:

*Type cutting.*—Terminal cuttings.

*Time to initiate roots.*—Summer: About 10 days at 22° C. Winter: About 12 days at 22° C.

*Time to develop roots.*—Summer: About 21 days at 22° C. Winter: About 26 days at 22° C.

*Rooting habit.*—Fine, freely branching.

Plant description:

*General appearance.*—Rounded; compact; full, dense and bushy; very freely and basally branching; upright and spreading; moderate growth rate; suitable for 10 to 15-cm pots.

*Plant height.*—About 13 cm from soil level to top of plant plane.

*Lateral branches.*—Quantity: About 28. Length: About 8 cm. Diameter: About 6 mm. Internode length: About 1.5 cm. Color: 59A.

*Foliage description.*—Quantity of leaves per lateral branch: About 23. Shape: Elliptic with acuminate tip and attenuate base. Length: About 11 cm. Width: About 3.5 cm. Texture: Smooth, glabrous. Margin: Serrulate with ciliation. Color: Young foliage, upper surface: 146A. Young foliage, lower surface: 144A. Mature foliage, upper surface: 131A. Mature foliage, lower surface: 138B. Veins, upper surface: Towards base, 60A, green overtones towards apex. Veins, lower surface: 60A. Petiole: Length: About 1.3 cm. Diameter: About 3 mm. Color: 60A.

Flower description:

*Flowering habit.*—Freely flowering. Flowers not persistent.

*Natural flowering season.*—Year-round. Plants flower about 8 weeks after planting. Flowers typically last less than one week depending on environmental and cultural conditions.

*Flowers borne.*—Flower buds develop in apical leaf axils. Open flowers are displayed above the foliage.

*Quantity of inflorescences.*—Freely flowering, usually about 100 flower buds and open flowers per plant.

*Flower shape.*—Rounded oval.

*Flower diameter.*—About 6 cm.

*Flower depth (height).*—About 1 cm.

*Petals.*—Shape: Obcordate with emarginate apex and acute base. Quantity, arrangement: Five petals overlapping. Aspect: Somewhat cupped. Length: About 2.7 cm. Width: About 3.5 cm. Texture: Smooth, shiny, and glabrous. Margin: Entire. Color: When opening, upper surface: 57D; eye, 57A. When opening, lower surface: 63B. Fully opened, upper surface: 57D; eye, 57A. Fully opened, lower surface: 63B.

*Peduncle.*—Angle: Erect. Strength: Slender, but strong. Length: About 5.7 cm. Color: 46A.

*Flower bud.*—Shape: Ovoid with spur. Length: About 1.8 cm. Diameter: About 1.1 cm. Color: 59B.

*Spur.*—Shape: Needle-shaped, curved at end. Length: About 5.2 cm. Color: 59A at apex to 59C at base.

*Reproductive organs.*—Androecium: Stamen number: 5. Anther shape: Oval. Anther size: About 5 mm. Anther color: 53B. Pollen color: 5D. Amount of pollen: Moderate. Gynoecium: Pistil length: About 8 mm. Style color: 141B. Stigma color: 149D. Ovary color: 139A.

Disease resistance: Resistance to pathogens common to New Guinea Impatiens has not been observed.

Seed development: Seed production has not been observed.

It is claimed:

1. A new and distinct variety of New Guinea Impatiens plant named 'Duepethopi', as illustrated and described.

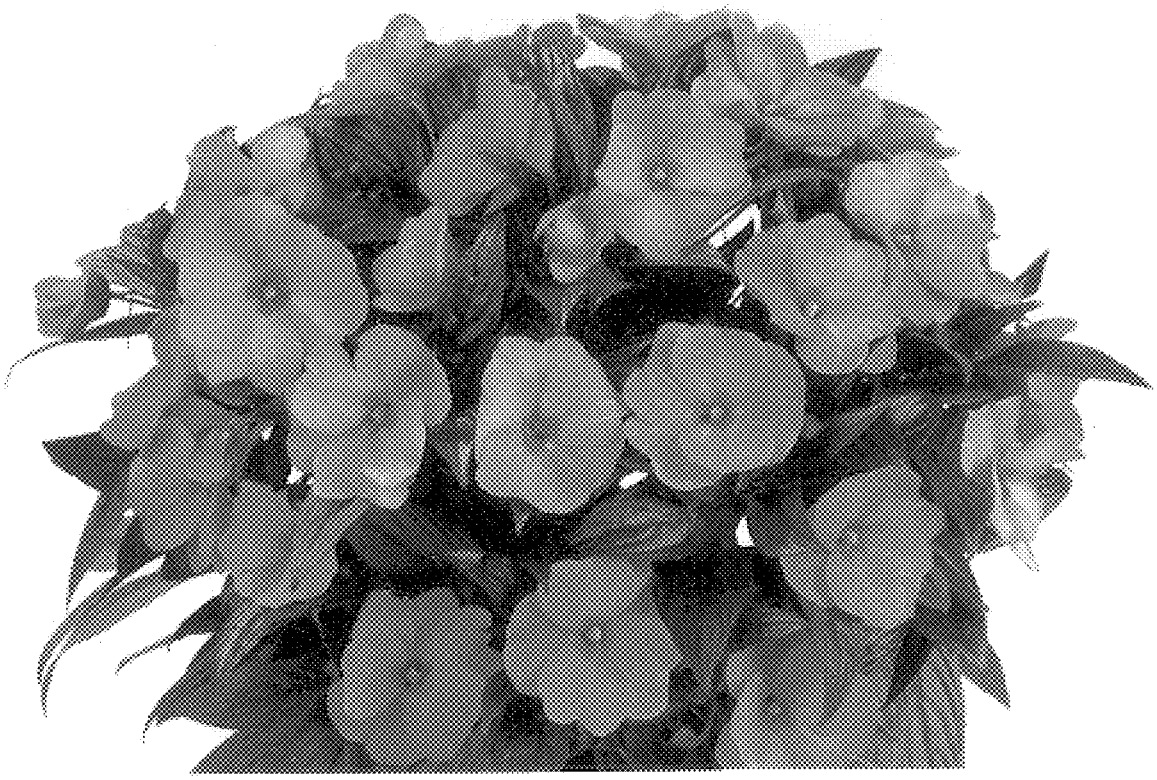

* * * * *